United States Patent
Lopez Villanueva et al.

(10) Patent No.: US 8,399,585 B2
(45) Date of Patent: Mar. 19, 2013

(54) PROCESS FOR PRODUCING WATER-ABSORBING POLYMER PARTICLES WITH IMPROVED BLOOD ABSORBANCE BY POLYMERIZING DROPLETS OF A MONOMER SOLUTION

(75) Inventors: Francisco Javier Lopez Villanueva, Mannheim (DE); Markus Linsenbühler, Ludwigshafen (DE); Rainer Dobrawa, Stuttgart (DE); Bernd Siegel, Otterstadt (DE); Matthias Weismantel, Jossgrund-Oberndorf (DE)

(73) Assignee: BASF SE, Ludwigshafen (DE)

( * ) Notice: Subject to any disclaimer, the term of this patent is extended or adjusted under 35 U.S.C. 154(b) by 52 days.

(21) Appl. No.: 12/861,227

(22) Filed: Aug. 23, 2010

(65) Prior Publication Data

US 2011/0071267 A1 Mar. 24, 2011

Related U.S. Application Data

(60) Provisional application No. 61/236,544, filed on Aug. 25, 2009.

(51) Int. Cl.
*C08F 20/06* (2006.01)

(52) U.S. Cl. ..................... 526/317.1; 502/402

(58) Field of Classification Search ............... 526/317.1
See application file for complete search history.

(56) References Cited

U.S. PATENT DOCUMENTS

| | | | |
|---|---|---|---|
| 4,020,256 A | 4/1977 | Zweigle et al. | |
| 6,150,477 A | 11/2000 | Engelhardt et al. | |
| 7,867,623 B2 * | 1/2011 | Ziemer et al. | 428/500 |
| 2002/0193546 A1 | 12/2002 | Freeman et al. | |
| 2009/0192035 A1 * | 7/2009 | Stueven et al. | 502/402 |

FOREIGN PATENT DOCUMENTS

| | | |
|---|---|---|
| DE | 3519013 A1 | 11/1986 |
| EP | 348 180 A2 | 12/1989 |
| EP | 0 816 383 A1 | 1/1998 |
| WO | WO-96/40427 A1 | 12/1996 |
| WO | WO-2005042024 A1 | 5/2005 |

OTHER PUBLICATIONS

BASF Technical Information on Lutensol® AT Surfactants (Jun. 2008).*
Buchholz, Fredric L., et al. (editors). "Solution Polymerization: Unit Operations and Their Effect on Product Quality." *Modern Superabsorbent Polymer Technology*. New York: John Wiley & Sons, Inc., 1998, pp. 71-103.

* cited by examiner

*Primary Examiner* — Vu A Nguyen
(74) *Attorney, Agent, or Firm* — Marshall, Gerstein & Borun LLP

(57) ABSTRACT

A process for producing water-absorbing polymer particles with improved blood absorbence by polymerizing droplets of a monomer solution in a surrounding gas phase, wherein the monomer solution comprises a surfactant.

9 Claims, No Drawings

PROCESS FOR PRODUCING WATER-ABSORBING POLYMER PARTICLES WITH IMPROVED BLOOD ABSORBANCE BY POLYMERIZING DROPLETS OF A MONOMER SOLUTION

CROSS-REFERENCE TO RELATED APPLICATIONS

This application claims the benefit of U.S. Provisional Patent Application No. 61/236,544, filed Aug. 25, 2009, incorporated herein by reference in its entirety.

The present invention relates to a process for producing water-absorbing polymer particles with improved blood absorbence by polymerizing droplets of a monomer solution in a surrounding gas phase, wherein the monomer solution comprises a surfactant.

The production of water-absorbing polymer particles is described in the monograph "Modern Superabsorbent Polymer Technology", F. L. Buchholz and A. T. Graham, Wiley-VCH, 1998, pages 71 to 103.

Being products which absorb aqueous solutions, water-absorbing polymers are used to produce diapers, tampons, sanitary napkins and other hygiene articles, but also as water-retaining agents in market gardening. Water-absorbing polymers are also referred to as "superabsorbent polymers" or "superabsorbants".

Spray polymerization allows the process steps of polymerization and drying to be combined. In addition, the particle size can be set within certain limits by a suitable process regime.

The preparation of water-absorbing polymer particles by polymerizing droplets of a monomer solution is described, for example, in EP 0 348 180 A1, EP 0 816 383 A1, WO 96/40427 A1, U.S. Pat. No. 4,020,256, US 2002/0193546 and DE 35 19 013 A1.

WO 2005/042042 A1 teaches that water-absorbing polymer particles are coated with surfactants and alcohols to improve blood absorbence.

It was an object of the present invention to provide an improved process for producing water-absorbing polymer particles with improved blood absorbence.

The object is achieved by a process for producing water-absorbing polymer particles by polymerizing droplets of a monomer solution comprising
a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a),
e) optionally one or more water-soluble polymers, and
f) water,
in a surrounding gas phase, the monomer solution comprising at least one surfactant.

The at least one surfactant may be an anionic, cationic and/or nonionic surfactant. Nonionic surfactants are preferred, especially nonionic surfactants with an HLB value of 2 to 18. The HLB value is a measure of the water or oil solubility of predominantly nonionic surfactants and can be determined by customary methods.

A surfactant consists of at least one nonpolar group and at least one polar group. Preferred surfactants have large nonpolar and/or polar groups. Large groups are groups with a molar mass of at least 130 g/mol, preferably at least 250 g/mol, more preferably at least 500 g/mol.

Suitable surfactants are, for example, sorbitan esters, such as sorbitan monostearate, sorbitan monooleate, sorbitan palmitate and sorbitan laurate, and also glyceryl esters whose acid component derives from C14- to C20-carboxylic acids.

Preferred surfactants are alkoxylated, preferably ethoxylated, alcohols, which alcohols may optionally be branched and/or saturated, and alkoxylated, preferably ethoxylated, sorbitan monoesters, such as sorbitan monostearate and sorbitan monooleate.

Very particularly preferred surfactants are ethoxylated C8-C20-alcohols.

The at least one surfactant preferably has a viscosity of more than 20 mPas, more preferably of more than 25 mPas, most preferably of more than 30 mPas (measured at 23° C. to EN 12092).

The amount of surfactant for use in the process according to the invention is preferably from 0.001 to 5% by weight, more preferably from 0.01 to 2% by weight, most preferably from 0.1 to 1% by weight, based in each case on the monomer a).

The addition of the surfactant to the monomer solution considerably enhances blood absorbance compared to the subsequent coating which has been customary to date, and significantly reduces the absorption time for blood.

The preparation of the typically water-insoluble water-absorbing polymer particles is explained in detail hereinafter.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids, such as acrylic acid, methacrylic acid, maleic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 2002/055469 A1, WO 2003/078378 A1 and WO 2004/035514 A1. A suitable monomer a) is, for example, acrylic acid purified according to WO 2004/035514 A1 comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The acid groups of the monomers a) are typically partly neutralized, preferably to an extent of at least 25 mol %, preferentially to an extent of from 50 to 80 mol %, more preferably to an extent of from 60 to 75 mol %, most preferably from 65 to 72 mol %, for which the customary neutralizing agents can be used, preferably alkali metal hydroxides, alkali metal oxides, alkali metal carbonates or alkali metal hydrogencarbonates, and mixtures thereof. Instead of alkali metal salts, it is also possible to use ammonium salts. Sodium and potassium are particularly preferred as alkali metals, but very particular preference is given to sodium hydroxide, sodium carbonate or sodium hydrogencarbonate and mixtures thereof. Typically, the neutralization is achieved by mixing in the neutralizing agent as an aqueous solution, as a melt, or preferably also as a solid. For example, sodium hydroxide with a water content significantly below 50% by weight may be present as a waxy material with a melting point above 23° C. In this case, metered addition as piece material or a melt at elevated temperature is possible. Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tartrates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), and Trilon® M (methylglycinediacetic acid).

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, preferably at least 10 ppm by weight, more preferably at least 30 ppm by weight, especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 2002/032962 A2.

Preferred crosslinkers b) are pentaerythrityl triallyl ether, tetraalloxyethane, methylenebismethacrylamide, 15 to 30-tuply ethoxylated glyceryl triacrylate, 15 to 30-tuply ethoxylated trimethylolpropane triacrylate, 15 to 20-tuply ethoxylated trimethylolethane triacrylate, 15 to 20-tuply ethoxylated trimethylolpropane triacrylate, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example, in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably from 0.01 to 1.5% by weight, more preferably from 0.05 to 1% by weight, most preferably from 0.1 to 0.6% by weight, based in each case on monomer a). With rising crosslinker content, the centrifuge retention capacity (CRC) falls and the absorption under a pressure of 21.0 g/cm$^2$ (AUL0.3 psi) passes through a maximum.

The initiators c) used may be all compounds which disintegrate into free radicals under the polymerization conditions, for example peroxides, hydroperoxides, hydrogen peroxide, persulfates, azo compounds and what are known as redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane]dihydrochloride and 2,2'-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxy-methylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof.

The initiators are used in customary amounts, for example in amounts of from 0.001 to 5% by weight, preferably from 0.01 to 2% by weight, based on the monomers a).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methylcellulose or hydroxyethylcellulose, gelatin, polyglycols or polyacrylic acids, preferably starch, starch derivatives and modified cellulose.

The water content of the monomer solution is preferably less than 65% by weight, preferentially less than 62% by weight, more preferably less than 60% by weight, most preferably less than 58% by weight.

The monomer solution has, at 20° C., a density of preferably from 1 to 1.3 g/cm$^3$, more preferably from 1.05 to 1.25 g/cm$^3$, more preferably from 1.1 to 1.2 g/cm$^3$.

The aqueous monomer solution is metered into a gas phase to form discrete droplets.

In the process according to the invention, it is possible to use one or more spray nozzles. The usable spray nozzles are not subject to any restriction. The liquid to be sprayed can be supplied to such nozzles under pressure. The liquid to be sprayed can be divided by decompressing it in the nozzle bore on attainment of a particular minimum velocity. In addition, it is also possible to use one-substance nozzles for the inventive purpose, for example slot nozzles or swirl chambers (full-cone nozzles) (for example from Düsen-Schlick GmbH, Germany, or from Spraying Systems Deutschland GmbH, Germany).

Preference is given in accordance with the invention to full-cone nozzles. Among these, preference is given to those having an opening angle of the spray cone of from 60 to 180°. Particular preference is given to opening angles of from 90 to 120°. The throughput per spray nozzle is appropriately from 0.1 to 10 m³/h, frequently from 0.5 to 5 m³/h.

The reaction can also be carried out in apparatus in which the monomer solution can fall freely in the form of monodisperse droplets. Suitable apparatus for this purpose is as described, for example, in U.S. Pat. No. 5,269,980.

Droplet generation by laminar jet decomposition, as described in Rev. Sci. Instr. 38 (1966) 502, is likewise possible.

The droplets can also be obtained by means of pneumatic draw dies, rotation, cutting of a jet, or rapidly actuable microvalve nozzles.

In a pneumatic draw die, a liquid jet together with a gas stream is accelerated through a diaphragm. The amount of gas can be used to influence the diameter of the liquid jet and hence the droplet diameter.

In the case of droplet generation by rotation, the liquid passes through the orifices of a rotating disk. The centrifugal force which acts on the liquid tears off droplets of defined size. Preferred apparatus for rotary dropletization is described, for example, in DE 43 08 842 A1.

However, the emerging liquid jet can also be cut into defined segments by means of a rotating blade. Each segment subsequently forms a droplet.

In the case of use of microvalve nozzles, droplets with defined liquid volume are obtained directly.

In a particularly preferred embodiment of the present invention, the monomer solution is metered into the reaction chamber by means of at least one bore to form droplets. The bores may be present, for example, in a dropletizer plate.

A dropletizer plate is a plate having at least one bore, the liquid entering the bore from the top. The dropletizer plate or the liquid can be oscillated, which generates a chain of ideally monodisperse droplets at each bore on the underside of the dropletizer plate. In a preferred embodiment, the dropletizer plate is not agitated.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The Reynolds number based on the throughput per bore and the bore diameter is preferably less than 2000, preferentially less than 1600, more preferably less than 1400 and most preferably less than 1200.

The dropletizer plate has typically at least one bore, preferably at least 10, more preferably at least 50 and typically up to 10000 bores, preferably up to 5000, more preferably up to 1000 bores, the bores typically being distributed uniformly over the dropletizer plate, preferably in so-called triangular pitch, i.e. three bores in each case form the corners of an equilateral triangle.

The separation of the bores is preferably from 1 to 50 mm, more preferably from 2.5 to 20 mm, most preferably from 5 to 10 mm.

The temperature of the monomer solution as it passes through the bore is preferably from 10 to 60° C., more preferably from 15 to 50° C., most preferably from 20 to 40° C.

A gas flows through the reaction chamber. The carrier gas can be conducted through the reaction chamber in cocurrent or in countercurrent to the free-falling droplets of the monomer solution, preferably in cocurrent, i.e. from the top downward. After one pass, the gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The oxygen content of the carrier gas is preferably from 0.5 to 15% by volume, more preferably from 1 to 10% by volume, most preferably from 2 to 7% by weight.

As well as oxygen, the carrier gas preferably comprises nitrogen. The nitrogen content of the gas is preferably at least 80% by volume, more preferably at least 90% by volume, most preferably at least 95% by volume.

The gas velocity is preferably adjusted such that the flow in the reaction chamber is directed, for example no convection currents opposed to the general flow direction are present, and is, for example, from 0.01 to 5 m/s, preferably from 0.02 to 4 m/s, more preferably from 0.05 to 3 m/s, most preferably from 0.1 to 2 m/s.

The gas flowing through the reaction chamber is appropriately preheated to the reaction temperature before entry into the reaction chamber.

The gas entrance temperature, i.e. the temperature with which the gas enters the reaction chamber, is preferably from 160 to 250° C., more preferably from 180 to 230° C., most preferably from 190 to 220° C.

Advantageously, the gas entrance temperature is controlled in such a way that the gas exit temperature, i.e. the temperature with which the gas leaves the reaction chamber, is from 100 to 180° C., more preferably from 110 to 160° C., most preferably from 120 to 140° C.

The reaction can be carried out under elevated pressure or under reduced pressure; preference is given to a reduced pressure of up to 100 mbar relative to ambient pressure.

The reaction offgas, i.e. the gas leaving the reaction chamber, may, for example, be cooled in a heat exchanger. This condenses water and unconverted monomer a). The reaction offgas can then be reheated at least partly and recycled into the reaction chamber as cycle gas. A portion of the reaction offgas can be discharged and replaced by fresh gas, in which case water and unconverted monomers a) present in the reaction offgas can be removed and recycled.

Particular preference is given to a thermally integrated system, i.e. a portion of the waste heat in the cooling of the offgas is used to heat the cycle gas.

The reactors can be trace-heated. In this case, the trace heating is adjusted such that the wall temperature is at least 5° C. above the internal reactor temperature and condensation on the reactor walls is reliably prevented.

The water-absorbing polymer particles can additionally be coated or remoistened for further improvement of the properties. Suitable coatings for dust binding are, for example, polyols, hyperbranched hydrophilic polymers, for example polyglycerol, and hydrophilic dendrimers. Suitable coatings for counteracting the undesired caking tendency of the polymer particles are, for example, fumed silica, for example Aerosil® 200, and surfactants, for example Span® 20 (sorbitan monolaurate), Rewoderm® S1333 (disodium ricinoleic monoethanolamidosulfosuccinate), and the surfactants disclosed in WO 2007/074108 A1. Particularly suitable are N-containing surfactants, cationic surfactants and nonionic surfactants. Suitable coatings for improving the color stability (yellowing stability) are, for example, reducing agents such as sodium hypophosphite, sodium sulfite, sodium hydrogensulfite, Brüggolite® FF6 and Brüggolite® FF7 (Brüggemann Chemicals; Heilbronn; Germany).

The present invention further provides water-absorbing polymer particles obtainable by the process according to the invention.

The inventive water-absorbing polymer particles preferably have the shape of partially indented hollow spheres and are approximately spherical, i.e. the polymer particles have a mean sphericity (mSPHT) of at least 0.84, preferably at least 0.86, more preferably at least 0.88, most preferably at least 0.9. The sphericity (SPHT) is defined as $$SPHT = \frac{4\pi A}{U^2}$$

where A is the cross-sectional area and U is the cross-sectional circumference of the polymer particles. The mean sphericity (mSPHT) is the volume-average sphericity.

The mean sphericity (mSPHT) can be determined, for example, with the Camsizer® image analysis system (Retsch Technolgy GmbH; Haan; Germany).

Polymer particles with relatively low mean sphericity (mSPHT) are obtained by inverse suspension polymerization when the particles are agglomerated during or after the polymerization.

The water-absorbing polymer particles produced by customary solution polymerization (gel polymerization) are ground and classified after drying to obtain irregular polymer particles. The mean sphericity (mSPHT) of these polymer particles is between approx. 0.72 and approx. 0.78.

The inventive water-absorbing polymer particles have a content of hydrophobic solvent of typically less than 0.005% by weight, preferably less than 0.002% by weight, more preferably less than 0.001% by weight, most preferably less than 0.0005% by weight. The content of hydrophobic solvent can be determined by gas chromatography, for example by means of the headspace technique.

Polymer particles which have been obtained by inverse suspension polymerization still typically comprise approx. 0.01% by weight of the hydrophobic solvent used as the reaction medium.

The inventive water-absorbing polymer particles have a blood absorbence of preferably at least 15 g/g, more preferably at least 18 g/g, most preferably at least 20 g/g. The blood absorbence is typically less than 40 g/g.

The inventive water-absorbing polymer particles have an absorption time for blood of preferably less than 7 seconds, more preferably less than 6 seconds, most preferably less than 5 seconds.

The mean diameter of the inventive water-absorbing polymer particles is preferably from 300 to 450 µm, more preferably from 320 to 420 µm, very particularly from 340 to 400 µm.

The inventive water-absorbing polymer particles have a moisture content of preferably from 5 to 20% by weight, more preferably from 7 to 18% by weight, most preferably from 10 to 16% by weight.

The present invention further provides hygiene articles which comprise the inventive water-absorbing polymer particles.

Hygiene articles are understood to mean especially sanitary napkins.

The water-absorbing polymer particles are tested by means of the test methods described below.

Methods

The measurements should, unless stated otherwise, be carried out at an ambient temperature of 23±2° C. and a relative air humidity of 50±10%. The water-absorbing polymer particles are mixed thoroughly before the measurement.

Blood Absorbence

Blood absorbence is determined by the EDANA recommended test method No. WSP 241.2-05 "Centrifuge Retention Capacity", except using, instead of a 0.9% by weight aqueous sodium chloride solution, sheep's blood modified according to U.S. Pat. No. 6,417,424 (column 17, line 33 to column 18, line 45).

Droplet Test

The droplet test determines the absorption time for blood. For the measurement, a layer of water-absorbing polymer particles of height approx. 1 mm is introduced. By means of an Eppendorf pipette, 0.1 ml of sheep's blood modified according to U.S. Pat. No. 6,417,424 is applied dropwise, and the time until disappearance of the droplet is measured. The mean of three measurements is calculated.

The EDANA test methods are, for example, obtainable from EDANA, Avenue Eugene Plasky 157, B-1030 Brussels, Belgium.

EXAMPLES

Example 1

18.3 kg of aqueous sodium acrylate solution (37.5% by weight solution in deionized water) and 2.1 kg of acrylic acid were mixed with 13.0 g of triethoxylated glyceryl triacrylate (approx. 85% by weight). The solution was inertized with nitrogen, such that the oxygen content fell to 6 ppm, and dropletized in a heated dropletization tower (height 12 m, width 2 m, gas velocity 0.1 m/s in cocurrent). The metering rate of the monomer solution was 20.5 kg/h; the temperature of the monomer solution was 25° C. The dropletizer plate had 20 ×200 µm bores. Upstream of the dropletizer, the initiator was metered into the monomer solution by means of static mixers. The initiator used was a 1.8% by weight aqueous solution of 2,2'-azobis[2-(2-imidazolin-2-yl)propane]dihydrochloride and a 3% by weight aqueous sodium peroxodisulfate solution. The metering rates of the initiator solutions were 1.031 kg/h and 0.619 kg/h respectively. The mixer and dropletizer were connected directly to one another. The heating output of the gas preheater was regulated such that the gas outlet temperature of the dropletization tower was 130° C. The resulting polymer particles were screened to a particle size of from 150 to 850 µm, in order to remove any agglomerates formed.

The resulting polymer particles were analyzed. The results are compiled in table 1.

Example 2

The procedure was as in example 1; together with the aqueous solution of 2,2'-azobis[2-(2-imidazolin-2-yl)propane]dihydrochloride, 19 g/h of Lutensol® AT80 (BASF SE; Ludwigshafen; Germany) were additionally metered into the monomer solution. Lutensol® AT80 is an ethoxylated alcohol based on a saturated linear C16-C18-fatty alcohol with approx. 80 ethylene oxide units.

The resulting polymer particles were analyzed. The results are compiled in table 1.

Example 3

The procedure was as in example 1; together with the aqueous solution of 2,2'-azobis[2-(2-imidazolin-2-yl)propane]dihydrochloride, 37 g/h of Lutensol® AT80 were additionally metered into the monomer solution.

The resulting polymer particles were analyzed. The results are compiled in table 1.

Example 4

800 g of polymer particles from example 1 were added at ambient temperature to a Pflugschar® M5 plowshare mixer with a heating jacket (Gebr. Lödige Maschinenbau GmbH, Paderborn, Germany). At 200 rpm of the mixer shaft, 10.9 g of a 15.0% by weight aqueous solution of Lutensol® AT80 were sprayed onto the polymer particles within 4 minutes. The mixer shaft speed was then reduced to 60 rpm and mixing was continued under these conditions for another 5 minutes. The coated polymer particles were discharged from the mixer and any agglomerates formed were screened off by means of a screen with a mesh size of 850 μm.

Example 5

The procedure was as in example 4, except that 21.9 g of the 15.0% by weight aqueous solution of Lutensol® AT80 were sprayed on.

TABLE 1

Results

| Example | Amount of surfactant based on acrylic acid | Blood absorption [g/g] | Droplet test [s] |
| --- | --- | --- | --- |
| 1*) | none | 6.8 | 7.0 |
| 2 | 0.25% by wt. | 16.0 | 5.3 |
| 3 | 0.5% by wt. | 20.7 | 4.0 |
| 4*) | 0.25% by wt. | 10.2 | 11.3 |
| 5*) | 0.5% by wt. | 10.4 | 11.0 |

*)Comparative examples

The invention claimed is:

1. Water-absorbing polymer particles obtained by polymerizing droplets of a monomer solution comprising
    (a) at least one ethylenically unsaturated monomer which bears acid groups and may be at least partly neutralized,
    (b) at least one crosslinker,
    (c) at least one initiator,
    (d) optionally one or more ethylenically unsaturated monomer copolymerizable with the monomer mentioned under (a),
    (e) optionally one or more water-soluble polymer,
    (f) water, and
    (g) at least one surfactant,
in a surrounding gas phase,
    said polymer particles having a mean sphericity of at least 0.84.

2. Polymer particles according to claim 1, wherein the acid groups of the monomer a) are neutralized to an extent of at least 25 mol %.

3. Polymer particles according to claim 1, wherein the monomer solution, based on the monomer a), comprises from 0.1% to 5% by weight of the at least one surfactant.

4. Polymer particles according to claim 1, wherein the at least one surfactant is an ethoxylated alcohol.

5. Polymer particles according to claim 1, wherein the monomer a) is acrylic acid to an extent of at least 50 mol %.

6. Polymer particles according to claim 1, which have a blood absorbence of at least 15 g/g.

7. Polymer particles according to claim 1, which have an absorption time for blood of less than 7 seconds, as determined using a droplet test in which modified sheep's blood is applied as a droplet to a layer of the polymer particles and a time until disappearance of the droplet is measured.

8. A hygiene article comprising water-absorbing polymer particles according to claim 1.

9. Polymer particles according to claim 6, which have an absorption time for blood of less than 7 seconds, as determined using a droplet test in which modified sheep's blood is applied as a droplet to a layer of the polymer particles and a time until disappearance of the droplet is measured.

* * * * *